United States Patent

Matji et al.

Patent Number: 5,597,847
Date of Patent: Jan. 28, 1997

[54] NITRIC ESTERS OF DERIVATIVES OF THE 2-(2,6-DI-HALO-PHENYLAMINO) PHENYLACETIC ACID AND PROCESS FOR THEIR PREPARATION

[75] Inventors: José A. Matji; Antonio Alcaide, both of Madrid, Spain

[73] Assignees: Corlay S.L., Madrid, Spain; Metgrove Ltd., Dublin, Ireland

[21] Appl. No.: 211,447

[22] PCT Filed: Jul. 20, 1993

[86] PCT No.: PCT/EP93/01906

§ 371 Date: Mar. 31, 1994

§ 102(e) Date: Mar. 31, 1994

[87] PCT Pub. No.: WO94/04484

PCT Pub. Date: Mar. 3, 1994

[30] Foreign Application Priority Data

Aug. 20, 1992 [IT] Italy ................ MI92A2006

[51] Int. Cl.⁶ .................. A61K 31/21; C07C 203/04
[52] U.S. Cl. .................. 514/509; 558/482; 558/483
[58] Field of Search .................. 560/43; 558/482, 558/483; 514/509

[56] References Cited

U.S. PATENT DOCUMENTS 3,558,690  1/1971  Sallmann et al. .................. 260/471

FOREIGN PATENT DOCUMENTS 3407507  9/1985  Germany.
91/06539  5/1991  WIPO.

*Primary Examiner*—Gary Geist
*Assistant Examiner*—Rosalynd A. Williams
*Attorney, Agent, or Firm*—Collard & Roe, P.C.

[57] ABSTRACT

Object of this invention are nitric esters of derivatives of the 2-(2,6-di-halophenylamino)phenylacetic acid, having the following general formula:

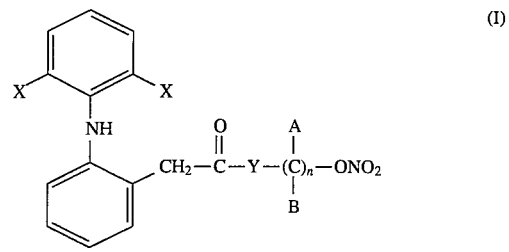

(I)

wherein: A and B are selected from among hydrogen and linear or branched, substituted or non substituted alkyl chains, X is a halogen selected from among chlorine and bromine, Y is selected from among oxygen, NH and $NR_1$, wherein $R_1$ is a linear or branched alkyl group, and n is comprised between 1 and 10 as well as their pharmaceutical utilization and process for their preparation.

14 Claims, No Drawings

NITRIC ESTERS OF DERIVATIVES OF THE 2-(2,6-DI-HALO-PHENYLAMINO) PHENYLACETIC ACID AND PROCESS FOR THEIR PREPARATION

This application is a 371 of PCT/EP93/01906, filed Jul. 20, 1993.

TECHNICAL FIELD

Object of the present invention are nitric esters of derivatives of 2-(2,6-di-halo-phenylamino)phenylacetic acid, their pharmaceutical utilization and process for their preparation.

PRIOR ART

The sodium salt of the 2-(2,6-di-chlorophenylamino)phenylacetic acid has been used for a long time in the pharmaceutical field for its anti-inflammatory activity and has been sold throughout the world for many years. The process for its preparation has been described in the Dutch Patent application No. 6.604.752 and in the U.S. Pat. No. 3,558,690.

The pharmacological profile and the effectiveness of the sodium salt of the 2-(2,6-di-chlorophenylamino)phenylacetic acid are described in Am.J.Med.80, Suppl. 4B, 1–87 (1986), while other data concerning its pharmacological activity as anti-inflammatory agent are reported, for instance, in C.A.74, 86215 m (1971); Krupp et al. Experimentia 29,450 (1973).

The utilization of the 2-(2,6-di-chlorophenylamino)phenylacetic acid as an anti-inflammatory preparation causes, as known, very severe adverse reactions, for instance in the gastro-intestinal apparatus, as well as damages to the liver and the kidneys. There exist numerous experimental evidences [S.MONCADA, R. M. J.PALMER, E. A.HIGGS, Pharmacological Reviews, 43(2), 109–142 (1991); T. F.LUSHER, C. M.BOULANGER, Y.DOHI, Z.YANG, Hypertension, 19, 117–130 (1992)], on whose basis the integrity of the vasal endothelium is assumed to act as a basically important protective barrier to prevent the onset of pathologic reactions in various organs and apparatuses.

Such protective barrier, and therefore the integrity of the vasal endothelium, is ensured, on the physiological plane, by the presence of nitric oxide and prostacyclin.

The treatment with drugs having an anti-inflammatory activity, such as, for instance, the sodium salt of the 2-(2,6-di-chloro-phenylamino)phenylacetic acid, causes the inhibition of the cyclo-oxygenase, an enzyme which governs the synthesis of the prostacyclin precursor. As a consequence, the production of prostacyclin being in this way inhibited, the tissular reserve of same is markedly depauperated, with ensuing compromission of the vasal endothelium.

As said, because of this endothelial damage due to the reduction of prostacyclin, diffuse pathologic reactions break out which affect the gastrointestinal apparatus, the kidneys and the liver.

OBJECTS OF THE INVENTION

Object of the present invention is to provide a product which, while ensuring the maintenance of the pharmacological activity characteristic of the known anti-inflammatory preparations, can also eliminate the adverse reactions caused by the treatment with said drugs.

Another object of the present invention is the realization of a process for the preparation of derivatives of the 2-(2,6-di-halo-phenylamino)phenylacetic acid having an anti-inflammatory activity and that are exempt from those adverse reactions that are typical of the anti-inflammatory drugs.

DESCRIPTION OF THE INVENTION

These and still other objects and advantages which shall appear from the following description are obtained by derivatives of the 2-(2,6-di-halophenylamino)phenylacetic acid, which derivatives, according to the present invention, have the following general formula:

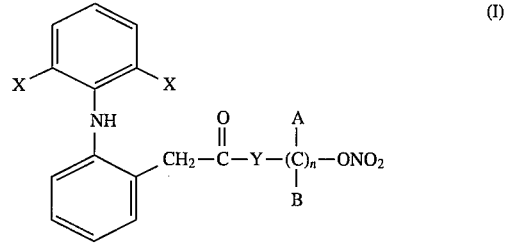

(I)

wherein:

A and B are selected among hydrogen, linear or branched, substituted or non substituted alkyl chains, X is a halogen selected among chloride and bromine, Y is selected among oxygen, NH, $NR_1$, wherein $R_1$ is a linear or branched alkyl group and n is comprised between 1 and 10.

In fact, it has been observed that the introduction of a group such as a terminal nitric ester in the derivatives of the 2-(2,6-di-halo-phenylamino)phenylacetic acid as in (I) permits to preserving the pharmacological activity of anti-inflammatory drugs, while eliminating the adverse reactions caused by the treatment with said drugs. The present invention also includes a pharmaceutical composition comprising an effective amount of a derivative 2-(2,6-di-halo-phenylamino)phenylacetic acid of formula (I) and an inert, non-toxic, pharmacologically acceptable carrier.

It has also been noticed that the derivatives (I) are useful for the treatment of different unhealthy conditions, such as for instance rheumatic diseases in general, immunologic disorders, and that they can also alleviate painful conditions of low-middle severity of any kind.

Besides, the derivatives (I) subject matter of the present invention are useful in the treatment of the illnesses of the cardiovascular apparatus and in particular in the treatment of myocardial and brain ischemiae, as well as in cases of arterial thrombosis.

Always according to the present invention, a nitric ester of a derivative of the 2-(2,6-di-halo-phenylamino)phenylacetic acid (I) proved to be especially advantageous, wherein:

A and B are hydrogen, X is chlorine, Y is oxygen, and n is equal to four, according to the following formula:

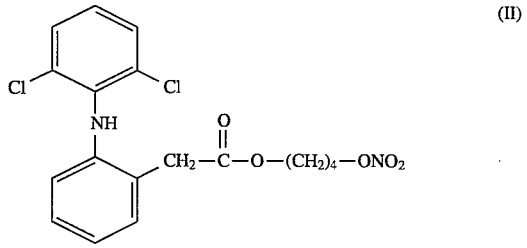

(II)

Also particularly advantageous according to this invention is a nitric ester of a derivative of the 2-(2,6-di-halo-phenylamino)phenylacetic acid (I),
wherein:

A and B are hydrogen, X is chlorine, Y is oxygen, and n is equal to two, according to the following formula:

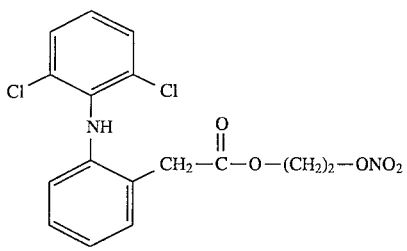

(III)

For the preparation of the derivatives (I) of the 2-(2,6-di-halo-phenylamino)phenylacetic acid subject matter of this invention, a first process proved to be particularly advantageous which, according to the present invention, comprises the following phases:

Reaction between the sodium salt of the 2-(2,6-di-halo-phenylamino)phenylacetic acid or of the 2-(2,6-di-halo-phenylamino)phenylacetic acid functionalized to the carboxylic group, and a compound having the following general formula:

(IV)

wherein:

$R_4$ is selected among chlorine, bromine, NHR in which R is hydrogen or linear or branched alkyl chain, A and B are selected among hydrogen, linear or branched, substituted or non substituted alkyl chains, $R_3$ is selected among chlorine, bromine and iodine, and n is comprised between 1 and 10, the carboxylic group of the 2-(2,6-di-halo-phenylamino)phenylacetic acid being functionalized as acylic chloride, anhydride or the like, obtaining in this way the corresponding monomer ester or the corresponding amide;

Reaction of said monomer ester or of said corresponding amide with a nitrating agent such as $AgNO_3$ or the like, obtaining in this way nitric esters of derivatives of the 2-(2,6-di-halo-phenylamino)phanylacetic acid (I).

A second process proved also particularly advantageous which, always according to the present invention, comprises the following phases:

Reaction between the sodium salt of the 2-(2,6-di-halo-phenylamino)phenylacetic acid or of the 2-(2,6-di-halo-phenylamino)phenylacetic acid functionalized to the carboxylic group, with a compound having the following general formula:

(V)

wherein:

$R_4$ is selected among chlorine, bromine, NHR in which R is hydrogen or linear or branched alkyl chains, A and B are selected among hydrogen, linear or branched, substituted or non substituted alkyl chains, and n is comprised between 1 and 10, the carboxylic group of the 2(2,6-di-halo-phenylamino)phenylacetic acid being functionalized as acylic chloride, anhydride or the like, obtaining in this way either the corresponding monomer ester or the corresponding amide;

Reaction of said monomer ester or said corresponding amide with an halogenating compound such as $PBr_3$ or the like, obtaining in this way said monomer ester or said amide, characterized by the presence of a terminal halogen group;

Reaction of said monomer ester or said amide, characterized by the presence of a terminal halogen group with a nitrating agent such as $AgNO_3$ or the like, obtaining in this way nitric esters of derivatives of the 2-(2,6-di-halo-phenylamino)phenylacetic acid (I). The solvents which are utilized in the processes subject matter of this invention are preferably selected among chloroform, methylene chloride, acetonitrile, dimethylformamide, tetrahydrofuran, dioxan and the like.

Such processes for the preparation of derivatives of the 2-(2,6-di-halo-phenylamino)phenylacetic acid (I), subject matter of the present invention, consist of a limited number of phases, allowing to obtain the products deriving from such processes rapidly, with satisfactory yields and to high amounts, even on an industrial basis.

According to the processes subject matter of this invention, the preparation of nitric esters of derivatives of the 2-(2,6-di-chloro-phenylamino)phenylacetic acid proved particularly advantageous, having the following formulae:

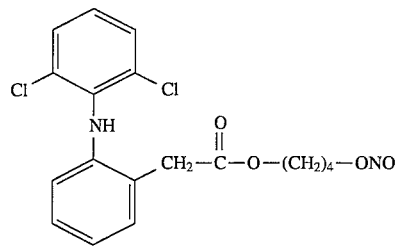

(II)

and

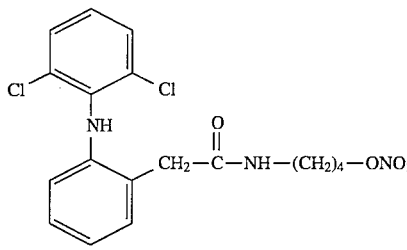

(XI)

which are prepared as described in the following examples, which are given as mere indications that do no limit in any way the protection scope of this invention.

EXAMPLE 1 a) 6 g of 1-Br-4-Cl-butane diluted in 250 ml of dimethylformamide were dripped to a solution of 10 g of sodium salt of the 2-(2,6-di-chloro-phenylamino)phenylacetic acid in 100 ml of dimethylformamide. The reaction mix was stirred for 12 hours at room temperature, then diluted with water and extracted with methylene chloride. The so extracted organic phase was anhydried on sodium sulfate and the solvent was low-pressure evaporated until 14 g of dry residual were obtained.

The residual was purified by chromatography on silica gel, utilizing chloroform as eluant system.

The head fractions were then collected, and by low-pressure evaporation of the solvent 11 g of dry residual were obtained and then chromatographed anew on silica gel, utilizing an eluant mix constituted by hexane/ether 7/3 (v/v).

The head fractions were collected, the solvent was low-pressure evaporated, and 3 g of 2-(2,6-di-chloro-phenylamino)phenylacetate of 4-chlorobutyl (VIII) were obtained.

IR (cm$^{-1}$): C=O, 1741; NH, 3340. $^1$H-NMR(300 MHz) (CDCl$_3$): 1.9 ppm(m, 4H); 3.6 ppm(m, 2H); 3.85 ppm(s, 2H); 4.2 ppm(m, 2H); 6.5–7.45 ppm(m, aromatics).

Mass spectrometry (i.e) : M$^+$385 b) 1.2 g of AgNO$_3$ diluted in 11 ml of acetonitrile were dripped to 2 g of (VIII) obtained as described in a), diluted in 7 ml of acetonitrile. The reaction mix was stirred for 12 hours at the temperature of 85° C. and then filtered.

The solvent was low-pressure evaporated from the resulting solution, and a residual was obtained to which 30 ml of methylene chloride were added. The mix so obtained was filtered anew, the organic phase was water-washed and then anhydried on sodium sulfate. The solvent was low-pressure evaporated and 2.8 g of dry residual were obtained, which were purified thereafter by chromatography on silica gel, utilizing an eluant mix constituted by hexane/ether 7/3 (v/v). The fractions containing the product were collected, the solvent was low-pressure evaporated and 2.5 g of nitric ester of 2-(2,6-chloro-phenylamino)phenylacetate of 4-hydroxybutyl (II) were obtained.

IR (cm$^{-1}$): C=O, 1729; NH, 3322; ONO$_2$, 1637. $^1$H-NMR(80 MHz) (CDCl$_3$): 1.75 ppm (m, 4H); 3.8 ppm (s, 2H); 4.2 ppm (m, 2H); 4.4 ppm (m, 2H); 6.45–7.4 ppm (m, aromatics).

Mass spectrometry (i. e.) M$^+$412

EXAMPLE 2 a) 0.5 g of ethylester of the 2-(2,6-di-chlorophenylamino)phenylacetic acid were added to 0.5 ml of 4-aminobutanol and the mix so obtained was stirred at the temperature of 100° C. for 12 hours. The mix was then brought again to room temperature, diluted with 5 ml of water and extracted with 5 ml of methylene chloride. The organic phase so extracted was anhydried on sodium sulfate and the solvent was low-pressure evaporated until 0.19 g of 2-(2,6-di-chloro-phenylamino)-4-hydroxybutyl-phenylacetamide (XII) were obtained.

IR (cm$^{-1}$) (nujol): C=O, 1648; NH and OH, 3413. $^1$H-NMR(80 MHz) (CDCl$_3$): 1.65 ppm (m, 4H); 3.3 ppm (m, 2H); 3.6 ppm (m, 2H); 6.08 ppm (m, 1H); 6.5 ppm (dd, 1H); 6.85–7.5 ppm (m, 6H).

Mass spectrometry: PM 366 b) 1.14 g of PBr$_3$ were added to a solution of 0.19 g of 2-(2,6-di-chloro-phenylamino)-4-hydroxybutyl-phenylacetamide (XII) in 10 ml of chloroform; the mix so obtained was stirred for 30 minutes and then diluted with 10 ml of water. The organic phase was separated and anhydried on sodium sulfate, and then the solvent was low-pressure evaporated, obtaining in this way a raw residual which was purified by chromatography, utilizing an eluant mix constituted by methylene chloride/ethyl acetate 10/0.1 (v/v).

The intermediate fractions were recovered, the solvent was low-pressure evaporated and 50 mg of 2-(2,6-di-chloro-phenylamino)-4-bromobutyl-phenylacetamide (XIII) were obtained.

$^1$H-NMR(80 MHz) (CDCl$_3$): 1.73 ppm (m, 4H); 3.3 ppm (m, 8H); 3.67 ppm (s, 2H); 5.91 ppm (broad s, 1H); 6.5 ppm (dd, 1H); 6.92–7.29 ppm (m, 5H); 7.4 ppm (d, 1H).

c) 1.5 g of AgNO$_3$ diluted in 10.7 ml of acetonitrile were added to a solution constituted by 2.8 g of 2-(2,6-di-chloro-phenylamino)-4-bromobutyl-phenylacetamide (XIII) diluted in 9 ml of acetonitrile. The reaction mix was stirred at the temperature of 25° C. for 3 days and then filtered. The solvent was low-pressure evaporated from the resulting solution, obtaining in this way a residual which was purified by chromatography, utilizing methylene chloride as eluant. The fractions containing the product were collected, the solvent was low-pressure evaporated, and 0.5 g of nitric ester of 2-(2,6-di-chloro-phenylamino)-4-hydroxybutylphenylacetamide (XI) were obtained.

IR(cm$^{-1}$) (nujol): C=O, 1650; NH, 3290; ONO$_2$, 1630. $^1$H-NMR (80 MHz) (CDCl$_3$): 1.62 ppm (m, 4H); 3.28 ppm (m, 2H); 4.4 ppm (t, 2H); 5.3 ppm (broad s, 1H); 6.4.9 ppm (dd, 1H); 6.85–7.36 ppm (m, 5H); 7.4 ppm (d, 1H).

Mass spectrometry: PM 411.

There has been determined by means of biologic tests, the anti-inflammatory and analgesic activity for instance of derivatives of the 2-(2,6-di-halo-phenylamino)phenylacetic acid (I) having the following formulae:

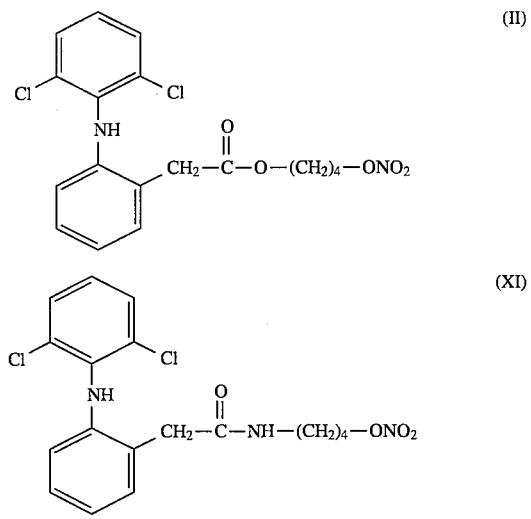

The anti-inflammatory activity of said derivatives of the 2-(2,6-di-chloro-phenylamino)phenylacetic acid has been determined in Wistar rats, by utilizing the method of the carrageenan edema, as reported in C. A.WINTER, E.RISLEY, G. W.NUSS, Proc. Soc. Exp. Biol.Med. 111, 544–547 (1962), while the analgesic activity of said derivatives has been determined in Swiss mice, as reported by L. C.HENDERSHOT, J.FORSAITH, J.Pharmacol. Exp. Ter. 125, 237–249 (1959).

The anti-inflammatory and analgesic activity of said derivatives is given on Table 1, and is expressed as a power ratio relative to 2-(2,6-di-chlorophenylamino)phenylacetic acid taken as a reference.

Each value represents a mean of the values obtained by the treatment of 10 animals.

The compounds (II) and (XI) utilized for said biological tests were suspended in 0.5% carboxymethylcellulose before the administration.

TABLE 1

| COMPOUND | ANTI-INFLAMM. ACTIVITY | ANALGESIC ACTIVITY |
| --- | --- | --- |
| XI | 1.25 | 1.40 |
| II | 1.30 | 1.50 |
| 2-(2,6-di-chloro-phenylamino)phenyl-acetic acid | 1 | 1 |

Then, the acute toxicity of said derivatives (II) and (XI) was evaluated by oral administration of a single dose of each compound (II) and (XI), utilizing for each derivative groups of 10 Swiss mice. The lethality incidence and the onset of toxic symptoms were assessed within a period of observation of 14 days.

Even upon administration of 250 mg/kg of the compound (II) or the compound (XI) no apparent toxicity symptoms have been observed in the studied animals.

Further biological experiments, suitable to determine the pharmacotoxicologic profile of the derivative (II) have been carried out by examining said derivative (II) in comparison with the 2-(2,6-di-chlorophenylamino)phenylacetic acid taken as a reference.

A. PHARMACODYNAMIC ACTIVITY

Acute Models

RAT CARRAGEENAN PAW EDEMA: the values of ED 30 (mg/kg p.o.) obtained are respectively equal to 4.88 for the compound (II) and to 4.21 for the 2-(2,6-di-chlorophenylamino)phenylacetic acid, showing a comparable effectiveness between the two compounds.

MOUSE PHENYLQUINONE WRITHING: at doses ranging between 3 and 10 mg/kg p.o., the derivative (II) has shown a full effectiveness and its potency resulted almost comparable to that of the 2-(2,6-di-chlorophenylamino)phenylacetic acid and of indomethacin.

Subacute Models

RAT ADJUVANT ARTHRITIS: the animals treated for 19 consecutive days (from the 3rd to the 21th day after the adjuvant injection) with 3.0 mg/kg p.o. of 2-(2,6-di-chlorophenylamino)phenylacetic acid or with 1.5 or 3.0 mg/kg p.o. of the compound (III), have shown a significant reduction of the arthritic symptomatology.

Rat Gastrointestinal Tolerability

In all the animals treated with 15 mg/kg p.o. of 2-(2,6-di-chloro-phenilamino)phenylacetic acid, severe diffuse ulcerations have been observed; small ulcers have been observed also in animals treated with 3.5 and 7.0 mg/kg p.o.

The average dose of ulcerogenicity for the 2-(2,6-di-chloro-phenylamino)phenylacetic acid has been calculated as being equal to 6.1 mg/kg p.o.

The compound (II) showed to be very well tolerated even at much higher doses compared to the above mentioned ones; small ulcers have been noticed only in 2 animals out of 10, treated with 100 mg/kg. Therefore it was impossible to determine the average ulcerogenicity dose for the compound (II).

General Pharmacology

Secondary pharmacological evaluations of the compound (II) have been carried out by comparison with the 2-(2,6-di-chloro-phenylamino)phenylacetic acid; no additional effects have been observed besides the primary pharmacological activity on the central nervous system, the autonomic system, the cardiovascular, respiratory and gastrointestinal systems.

B. TOXICOLOGY

Acute Toxicity in Rodents

Studies have been carried out in two animal species and following two different administration routes.

The following values of LD50 (mg/kg) and of the 95% fiducial limits have been obtained: rat, oral route: 511 (356–732); mouse, oral route: 497 (323–762); rat, intraperitoneal route: 237 (156–359); mouse, intraperitoneal route: 253 (171–374).

Maximum Tolerated Dose in Non-Rodents

The compound (II) was very well tolerated in this animal species which, as known, is particularly sensitive to this class of compounds.

The animals have been treated with doses increasing from 250 to 1000 mg/kg of compound (II): the lowest dose caused no symptomatology, the intermediate dose caused only a reversible diarrhea, while the highest dose caused a severe but reversible diarrhea. On the contrary, the administration in the same conditions of 10 mg/kg of 2-(2,6-di-chlorophenylamino)phenylacetic acid caused the death of the animals.

Subacute Toxicity in Rodents

The animals have been treated with 5, 15 and 30 mg/kg of compound (II) for 4 weeks. The general conditions and clinical behaviour, body weight gain, water and food consumption, hematology and clinical chemistry have shown that the two lowest doses have been well tolerated.

Subacute Toxicity in the Dog

The animals have been treated with 5, 15 and 30 mg/kg of compound (II) for 4 weeks. The general conditions and clinical behaviour, body weight gain, water and food consumption, hematology and clinical chemistry have shown that the two lowest doses have been well tolerated.

We claim:

1. Derivatives of the 2-(2,6-di-halo-phenylamino)phenylacetic acid, characterized in that they lave the following general formula:

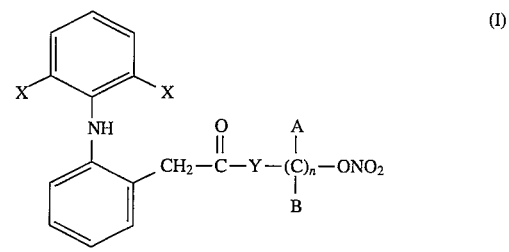

wherein:
A and B are selected among hydrogen, linear or branched, substituted or non substituted alkyl chains, X is halogen selected among chlorine and bromine, Y is selected among oxygen, NH, NR$_1$, wherein R$_1$ is a linear or branched alkyl group, and n is comprised between 1 and 10.

2. A derivative of the 2-(2,6-di-halophenylamino)phenylacetic acid according to claim 1, characterized in that X is chlorine, A and B are hydrogen, Y is oxygen and n is equal to 4.

3. A derivative of the 2-(2,6-di-halophenylamino)phenylacetic acid according to claim 1, characterized in that X is chlorine, A and B are hydrogen, Y is oxygen and n is equal to 2.

4. A derivative of the 2-(2,6-di-halophenylamino)phenylacetic acid according to claim 1, characterized in that X is chlorine, A and B are hydrogen, Y is NH and n is equal to 4.

5. A process for the preparation of a derivative of 2-(2,6-di-halo-phenylamino) phenylacetic acid, having the following formula (I):

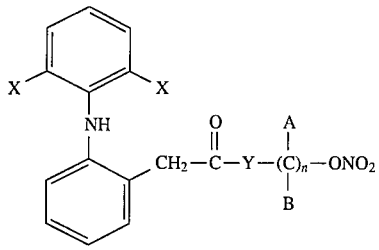

wherein:

A and B are selected among hydrogen, linear and branched, substituted and non-substituted alkyl chains, X is halogen selected among chlorine and bromine, Y is selected among oxygen, NH, $NR_1$, wherein $R_1$ is a linear or branched alkyl group and n is comprised between 1 and 10, comprising:

reaction between the sodium salt of the 2-(2,6-di-halo-phenylamino)phenylacetic acid or of the 2-(2,6-di-halo-phenylamino)phenylacetic acid functionalized to the carboxylic group, with a compound having the following formula (IV):

wherein:

$R_4$ is selected among chlorine, bromine, NHR in which R is hydrogen or linear or branched alkyl chain, A and B are selected among hydrogen, linear or branched, substituted or non-substituted alkyl chains, $R_3$ is selected among chlorine, bromine and iodine, and n is comprised between 1 and 10, the carboxylic group of the 2-(2,6-di-halo-phenylamino)phenylacetic acid being functionalized as acylic chloride, or anhydride, obtaining in this way the corresponding monomer ester or the corresponding amide;

reaction of said monomer ester or said amide with a nitrating agent, obtaining in this way nitric esters of derivatives of the 2-(2,6-di-halo-phenylamino)phenylacetic acid (I).

6. Process for the preparation of a derivative of a 2-(2,6-di-halophenylamino)phenylacetic acid, having the following formula (I):

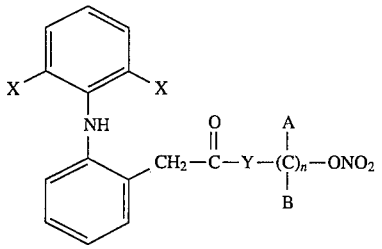

wherein:

A and B are selected among hydrogen, linear and branched, substituted and non-substituted alkyl chains, X is a halogen selected among chlorine and bromine, Y is selected among oxygen, NH, $NR_1$, wherein $R_1$ is a linear or branched alkyl group and n is comprised between 1 and 10, comprising:

reaction between the sodium salt of the 2-(2,6-di-halophenylamino)phenylacetic acid or of the 2-(2,6-di-halo-phenylamino)phenylacetic acid functionalized carboxylic group, with a compound having the following formula (V):

wherein:

$R_4$ is selected among chlorine, bromine, NHR in which R is hydrogen or linear or branched alkyl chain, A and B are selected among hydrogen, linear or branched, substituted or non-substituted alkyl chains, and n is comprised between 1 and 10, the carboxylic group of the 2-(2,6-di-halo-phenylamino)phenylacetic acid being functionalized as acylic chloride, or anhydride, obtaining the corresponding monomer ester or the corresponding amide;

reaction of said monomer ester or said amide with a halogenating compound, obtaining in this way said monomer ester or said amide, having a terminal halogen group;

reaction of said monomer ester or said amide having a terminal halogen group with a nitrating agent, obtaining in this way nitric esters of derivatives of the 2-(2,6-di-halo-phenylamino)phenylacetic acid (I).

7. A pharmaceutical composition comprising an effective therapeutic amount of a derivative of a 2-(2,6-di-halo-phenylamino)phenylacetic acid according to claim 1; and an inert, non-toxic, pharmacologically acceptable carrier.

8. A therapeutic method for treating rheumatic diseases in a warm-blooded animal comprising administering to said warm-blooded animal an effective amount of a derivative of a 2-(2,6-di-halo-phenylamino) phenylacetic acid according to claim 1.

9. A therapeutic method for treating cardiovascular illnesses in a warm-blooded animal comprising administering to said warm-blooded animal an effective amount of a derivative of a 2-(2,6-di-halo-phenylamino) phenylacetic acid according to claim 1.

10. A therapeutic method for treating miocardial and brain ischemiae in a warm-blooded animal comprising administering to said warm-blooded animal an effective amount of a derivative of a 2-(2,6-di-halo-phenylamino) phenylacetic acid according to claim 1.

11. A therapeutic method for treating arterial thrombosis in a warm-blooded animal comprising administering to said warm-blooded animal an effective amount of a derivative of a 2-(2,6-di-halo-phenylamino) phenylacetic acid according to claim 1.

12. The process as claimed in claim 5, wherein said nitrating agent is $AgNO_3$.

13. The process as claimed in claim 6, wherein said halogenating compound is $PBr_3$.

14. The process as claimed in claim 6, wherein said nitrating agent is $AgNO_3$.

* * * * *